United States Patent [19] [11] 4,081,595
Nagata et al. [45] Mar. 28, 1978

[54] REDUCTION GIVING 3-CEPHEM COMPOUNDS

[75] Inventors: Wataru Nagata, Nishinomiya; Masayuki Narisada, Ibaraki; Yoshio Hamashima, Kyo; Kyoto Okada, Osaka, all of Japan

[73] Assignee: Shionogi & Co., Ltd., Osaka, Japan

[21] Appl. No.: 740,967

[22] Filed: Nov. 11, 1976

[30] Foreign Application Priority Data

Nov. 11, 1975 Japan .................. 50-135385

[51] Int. Cl.² ............... C07D 501/04; C07D 501/60
[52] U.S. Cl. ............................ 544/23; 544/29; 544/16
[58] Field of Search ...................... 260/243 C

[56] References Cited
U.S. PATENT DOCUMENTS 3,883,518  5/1975  Ponticello et al. ............ 260/243 C
3,929,775  12/1975  Ochiai et al. ................ 260/243 C Primary Examiner—Donald G. Daus
Assistant Examiner—Jose Tovar
Attorney, Agent, or Firm—Birch, Stewart, Kolasch and Birch

[57] ABSTRACT

Antibacterial cephems having the following formula:

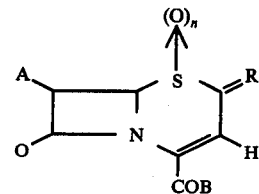

(wherein A is amino or substituted amino;
COB is carboxy or protected carboxy;
R is two hydrogens, hydrogen and a monovalent substituent, or a divalent substituent; and
$n$ is zero or one)

are prepared by reducing a compound having the following formula:

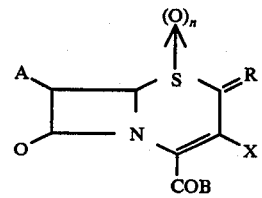

(wherein A, COB, R, and $n$ are as defined above and X is halo or sulfonyloxy)

with a reducing reagent.

6 Claims, No Drawings

REDUCTION GIVING 3-CEPHEM COMPOUNDS

This invention relates to a reduction for preparing antibacterial cephem compounds. More specifically, it relates to a process for preparing 7-(substituted or unsubstituted)amino-3-cephem-4-carboxylic acids or their derivatives at the carboxy (I) by reacting 3-halo- or 3-sulfonyloxy-7-(substituted or unsubstituted)amino-3-cephem-4-carboxylic acids or their derivatives at the carboxy (II) with a reducing reagent according to the following reaction scheme:

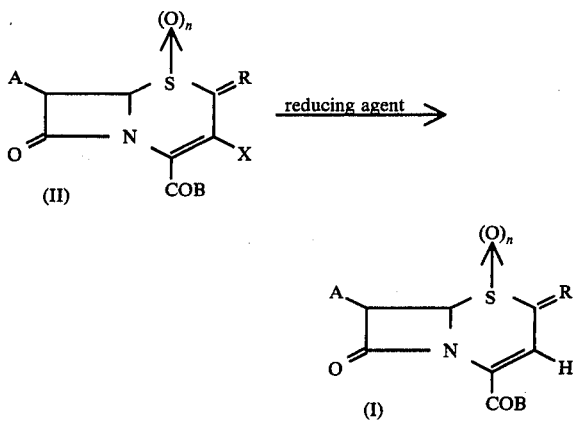

(wherein A is amino or substituted amino;
COB is carboxy or protected carboxy;
R is two hydrogens, hydrogen and a monovalent substituent, or a divalent substituent;
X is halo or sulfonyloxy; and
$n$ is zero or one).

Organic A, COB, R, and X can contain preferably 1 to 20 carbon atoms.

Substituents of 7-substituted amino for A of the Compounds (I) and (II) include amino protecting groups having side chains of natural or synthetic penicillins and cephalosporins, and their equivalents (e.g. acyl, silyl, sulfenyl, hydrocarbyl).

Acyls for said amino protecting groups A include carbonic acyl (e.g. alkoxycarbonyl, aralkoxycarbonyl, aryloxycarbonyl), sulfuric acyl, phosphoric acyl (e.g. dialkoxyphosphinyl, dialkoxythiophosphonyl, alkoxyaminophosphoroyl), and other inorganic acyls; alkanoyl, cycloalkanoyl, aralkanoyl, aroyl, alkylsulfonyl, arylsulfonyl, alkylphosphonyl, and other organic acyls. These groups, where possible, may have a hetero atom in the main chains, unsaturation or a substituent, e.g., a halogen (e.g. fluorine, chlorine, bromine), nitrogen function (e.g. amino, hydrazino, azido, alkylamino, arylamino, acylamino, alkylideneamino, acylimino, nitro), oxygen function (e.g. hydroxy, alkoxy, aralkoxy, aryloxy, acyloxy, oxo), sulfur function (e.g. mercapto, alkylthio, aralkylthio, arylthio, acylthio, thioxo, sulfo, sulfonyl, sulfinyl, alkoxysulfonyl, aryloxysulfinyl), carbon function (e.g. alkyl, alkenyl, aralkyl, aryl, carboxy, carboalkoxy, carbamoyl, alkanoyl, aroyl, aminoalkyl, aralkanoyl, cyano), phosphor function (e.g. phospho, phosphoroyl), or like functions. Further, these acyls can be diacyl groups (e.g. phthaloyl, pyridine-2,3-dicarbonyl, maleoyl, succinoyl) derived from polybasic acids.

Representative acyls include:
(1) alkanoyl;
(2) haloalkanoyl;
(3) azidoacetyl;
(4) cyanoacetyl;
(5) acyls of the formula:

Ar—CQQ'—CO—

(wherein Q and Q' each is hydrogen or methyl; Ar is phenyl, dihydrophenyl, or a monocyclic heterocyclic aromatic group containing 1 to 4 hetero atoms selected from nitrogen, oxygen, and/or sulfur atoms, each optionally substituted by e.g. alkyl, alkoxy, halogen, trifluoromethyl, hydroxy, cyano, aminomethyl, nitroso, nitro);
(6) acyls of the formula:

Ar—G—CQQ'—CO—

(wherein Ar, Q and Q' are as defined above, and G is oxygen or sulfur);
(7) acyls of the formula;

Ar—CHT—CO—

(wherein Ar is defined above and T is as
i) amino; ammonio; amino protected by a usual amino protecting group (e.g. benzyloxycarbonyl, alkoxycarbonyl, cyclopentyloxycarbonyl, cyclohexyloxycarbonyl, benzhydryloxycarbonyl, cyclopropylmethoxycarbonyl, methanesulfonylethoxycarbonyl, 2,2,2-trichloroethoxycarbonyl, guanidylcarbonyl, substituted ureidocarbonyl, alkanoyl, pyronecarbonyl, thiopyronecarbonyl, pyridonecarbonyl, aromatic carbocyclic or heterocyclic acyl optionally substituted by e.g. halogen, trifluoromethyl, alkyl, aminoalkyl, hydroxyalkyl; trityl); protected amino groups in the form of a phthalimido; or enamino (derived from e.g. amino and acetoacetate ester, acetylacetone, acetoacetonitrile);
(ii) hydroxyl, alkoxy, or acyloxy;
(iii) carboxy, alkoxycarbonyl, indanyloxycarbonyl, phenoxycarbonyl; or
(iv) azido, cyano, carbamoyl, sulfo, alkoxysulfonyl, alkoxyphosphonyl;
(8) 2-sydnon-3-alkanoyl;
(9) (2- or 4-pyridon-1-yl)alkanoyl;
(10) 5-aminoadipoyl, 5-aminoadipoyl protected at the amino or carboxy; or
(11) acyls of the formula:

L—0—CO—

(wherein L is an easily removable hydrocarbyl e.g. 2,2,2-trichloroethyl, isobornyl, t-butyl, 1-methylcyclohexyl, 2-alkoxyt-butyl, benzyl, p-nitrobenzyl, p-methoxybenzyl).

Typical examples of Ar in the said definition include furyl, thienyl, pyrryl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, phenyl, pyridyl, pyrimidyl, pyrazinyl, pyridazinyl, triazinyl, and dihydrophenyl, and each can optionally be substituted (by e.g. halogen, alkyl, hydroxy, aminomethyl, alkoxy).

Silyl (e.g. trialkylsilyl) and sulfenyl (e.g. phenylsulfenyl, o-nitrophenylsulfenyl) are usual amino protecting groups.

The hydrocarbyls for said amino protecting groups A include easily removable aliphatic hydrocarbyls (e.g. alkyl, alkenyl, aralkyl) and monocyclic aryls optionally substituted (by e.g. halogen, nitrogen, oxygen, sulfur, carbon, phosphor function).

These hydrocarbyls can be divalent hydrocarbyls (e.g. alkylene, aralkylene, alkylidene, aralkylidene, α-halo or alkoxy-aralkylidene, diarylmethylidene, cycloalkylidene).

Further, two amino substituents being an acyl and a hydrocarbyl, can be combined to form a ring structure (e.g. 4-oxo-3-imidazolidinyl ring). As mentioned above, these groups can also have substituents or unsaturation.

Preferable acylamino A containing said acyls are optionally substituted mandeloylamino, phenoxyacetamido, phenylacetamido, optionally protected α-phenylglycinamido, or 2-thienylacetamido.

Representative derivatives at the carboxy for COB include esters [such as alkyl (e.g. methyl-, ethyl-, trichloroethyl-esters), aralkyl (e.g. benzyl-, methoxybenzyl-, nitrobenzyl-, diphenylmethyl-, trityl-esters), aryl (e.g. phenyl-, naphthyl-, indanyl-esters), metal (e.g. trimethylsilyl-, trimethylstannyl-esters) esters], acid anhydrides, salts (e.g. sodium-, potassium-, magnesium-, aluminum-salts), thiol esters, amides, hydrazides, and azides.

Said COB moieties can, where possible, possess a substituent (e.g. halogen, sulfur-, oxygen-, nitrogen-, carbon-functions) or can be unsaturated.

Among these carboxy derivatives, important derivatives are those inert to the reaction and removable after the reaction without adverse effect on the other part of the molecule including substituents (e.g. haloalkyl-, acylalkyl, alkoxyalkyl-, acylalkyl, aralkyl-esters, dialkylhydrazides, alkali metal salts, alkylamino-salts).

Preferable COB are benzhydryloxycarbonyl, carboxy, p-methoxybenzyloxycarbonyl, p-nitrobenzyloxycarbonyl, and 2,2,2-trichloroethoxycarbonyl.

Compounds (I) and (II) can have a hydrogen and monovalent substituent (e.g. optionally substituted alkyl) or a divalent substituent (e.g. optionally substituted alkylene) for R.

Preferable R is two hydrogens; methyl and hydrogen; (5-methyl-1,3,4-thiadiazol-2-yl ) thiomethyl and hydrogen; or methylene.

Preferable examples of the sulfonyloxy for X are aliphatic and aromatic sulfonyloxy groups (e.g. methanesulfonyloxy, ethanesulfonyloxy, benzenesulfonyloxy, bromobenzenesulfonyloxy, naphthalenesulfonyloxy, toluene-p-sulfonyloxy), and of the halogen for X include chlorine, bromine, and iodine.

More preferable X are methanesulfonyloxy, toluene-p-sulfonyloxy, chlorine, and bromine.

Compounds (II) are available by treating the corresponding 3-hydroxy compounds with a halogenating agent (e.g. thionyl halide, oxalyl halide, phosphorous trihalide) or sulfonylating agent (e.g. alkanesulfonyl halide, arylsulfonyl halide), if required in the presence of base.

When Compounds (II) have a group susceptible to undesirable change during the reduction, it may be protected with a suitable protecting group prior to the reduction, and is deprotected at any stage after completion of the reduction. Many protections of various categories are known and used in the art.

Compounds (II) having an alkyl at position 2 can be prepared by introducing an alkyl by such conventional methods as alkylation of reactive hydrogen, and optionally modifying substituents at other positions. For example, compounds having alkyl at position 2 are available by reacting a cephem-1-oxide having no alkyl in position 2 with an alkylating agent e.g. alkyl halide and a strong base.

This invention is carried out by reducing Compounds (II) with a reducing reagent. The reducing reagent used for this reduction are those which can substitute a halogen or sulfonyloxy linked to a double bond with a hydrogen. Preferably, e.g. 0.5 to 10 parts by weight (to that of the starting material) of reducing metals (e.g. sodium, potassium, calcium, zinc, magnesium, aluminum) can be used alone or in forms of an amalgam or alloy together with e.g. 1 mole equivalent or more of water, alcohol (e.g. methanol, ethanol, glycol), acid (e.g. acetic acid, mineral acids) or alkali (e.g. sodium hydroxide) at 0° C to 100° C for 0.5 to 20 hours. Alternatively, the reduction can also be done using e.g. 0.1 to 5 parts by weight (to the starting material) of catalyzers for hydrogenation (e.g. platinum, palladium, nickel catalyzer) and 0.8 to 1.2 atm. hydrogen at 0° C to 100° C, or 1.0 mole or more of reducing metal salts (e.g. stannous chloride). The reduction can be carried out in a solvent (e.g. halohydrocarbon, ether, ester, acid solvents).

Compounds (II) can be treated with iodides (e.g. sodium iodide, potassium iodide) to produce 3-iodo cephems prior to the reduction.

Compounds (I) thus formed can be separated from unreacted starting materials, by-products, solvents, etc. by usual methods (e.g. extraction, filtration, drying, concentration, crystallization), and purified by conventional methods (e.g. recrystallization, reprecipitation, chromatography, countercurrent distribution).

The products of this invention are potential antibacterials useful for drugs for preventing or treating bacterial infection and disinfection as is described in Japanese Patent Application (Open to Public Inspection No. 591/1973).

This invention is further explained by reference to the following examples which are not given for restricting the scope of this invention.

EXAMPLE 1

To benzhydryl 3-chloro-7-phenylacetamido-3-cephem-4-carboxylate (1.038 g) in a mixture of acetic acid (30 ml) and methylene chloride (10 ml) one adds activated zinc powder (3.9 g), stirs at room temperature for 1 hour, filters, dilutes with water, extracts with methylene chloride, washes with water, dries, concentrates, and crystallizes from ether to give benzhydryl 7-phenylacetamido-3-cephem-4-carboxylate (865 mg), m.p. 168°–170° C.

Similarly, the following compounds are prepared from the corresponding 3-toluenesulfonyloxy-, 3-methanesulfonyloxy-, 3-chloro-, and 3-bromo-compound, respectively;
(1) 7-amino-3-cephem-4-carboxylic acid,
  m.p. 215° C (dec.);
(2) benzhydryl 7-amino-3-cephem-4-carboxylate,
  mp. 153°–154° C;
(3) 7-phenylacetamido-3-cephem-4-carboxylic acid,
  mp. 193°–196° C;
(4) benzhydryl 7-phenylacetamido-3-cephem-4-carboxylate-1-oxide,
  mp. 160° C (dec.);
(5) p-methoxybenzyl 7-phenylacetamido-3-cephem-4-carboxylate;
(6) 7-phenylacetamido-2-methyl-3-cephem-4-carboxylic acid, mp. 109°-115° C (dec.);
(7) benzhydryl 7-phenylacetamido-2-methyl-3-cephem-4-carboxylate;
(8) p-nitrobenzyl 7-phenylacetamido-2-methyl-3-cephem-4-carboxylate;
(9) p-nitrobenzyl 7-phenylacetamido-2-methyl-3-cephem-4-carboxylate-1-oxide;
(10) 7-phenylacetamido-2-methylene-3-cephem-4-carboxylic acid,
Rf: 0.70 (ethyl acetate : acetic acid : water = 8 : 1 : 1 /silica gel plate);
(11) benzhydryl 7-phenylacetamido-2-methylene-3-cephem-4-carboxylate;
(12) 7-phenylacetamido-2-methylene-3-cephem-4-carboxylic acid 1-oxide,
mp. 197°-200° C;
(13) benzhydryl 7-phenylacetamido-2-methylene-3-cephem-4-carboxylate-1-oxide,
mp. 152° C (dec.);
(14) 7-phenylacetamido-2-(5-methyl-1,3,4-thiadiazol-2-ylthio)methyl-3-cephem-4-carboxylic acid,
mp. 125°-131° C;
(15) benzhydryl 7-phenylacetamido-2-(5-methyl-1,3,4-thiadiazol-2-ylthio)methyl-3-cephem-4-carboxylate,
IR: $\nu_{max}^{CHCl_3}$ 3430, 1798, 1730, 1690 cm$^{-1}$;
(16) benzhydryl 7-phenylacetamido-2-(5-methyl-1,3,4-thiadiazol-2-ylthio)methyl-3-cephem-4-carboxylate-1-oxide;
(17) 7-(2-thienyl)acetamido-3-cephem-4-carboxylic acid,
mp. 174°-175° C;
(18) benzyhdryl 7-(2-thienyl)acetamido-3-cephem-4-carboxylate,
mp. 166°-167° C;
(19) 2,2,2-trichloroethyl 7-thienylacetamido-2-methyl-3-cephem-4-carboxylate,
mp. 118°-122° C;
(20) 7-(α-phenylglycinamido)-2-methyl-3-cephem-4-carboxylic acid
mp. 166°-171° C;
(21) 7-(α-phenylglycinamido)-3-cephem-4-carboxylic acid,
mp. 180°-210° C (dec.);
(22) benzhydryl 7-(N-t-butoxycarbonyl-α-phenylglycinamido-3-cephem-4-carboxylate,
mp. 126°-128° C; and
(23) 7-O-formylmandelamido-2-methyl-3-cephem-4-carboxylic acid,
IR: $\nu_{max}^{CHCl_3}$ 3300, 1786, 1723, 1680 cm$^{-1}$.

PREPARATION 1

(I) To benzhydryl 7-(2-thienyl)acetamido-3-cephem-4-carboxylate (98 mg) in methylene chloride (2 ml), one adds anisole (0.13 ml) and trifluoroacetic acid (0.26 ml) under ice cooling, stirs for 30 minutes at room temperature, concentrates to dryness, and crystallizes from ether to give 7-(2-thienyl)-acetamido-3-cephem-4-carboxylic acid (32 mg). mp. 174°-175° C (dec.).

Similarly, the following compounds are prepared from the corresponding benzhydryl ester.
(1) 7-phenylacetamido-3-cephem-4-carboxylic acid,
mp. 193°-196° C;
(2) 7-phenylacetamido-2-methyl-3-cephem-4-carboxylic acid,
mp. 109°-115° C (dec.);
(3) 7-phenylacetamido-2-methylene-3-cephem-4-carboxylic acid,
Rf: 0.70 (ethyl acetate : acetic acid : water = 8 : 1 : 1/silica gel plate);
(4) 7-phenylacetamido-2-(5-methyl-1,3,4-thiadiazol-2-ylthio)methyl-3-cephem-4-carboxylic acid,
mp. 125°-131° C;
(5) 7-(α-phenylglycyl)amino-3-cephem-4-carboxylic acid,
mp. 180°-210° C (dec.);
(6) 7-(α-phenylglycinamido)-2-methyl-3-cephem-4-carboxylic acid,
mp. 166°-171° C;
(7) 7-thienylacetamido-2-methyl-3-cephem-4-carboxylic acid,
mp. 175°-184° C;
(8) 7-O-formylmandelamido-2-methyl-3-cephem-4-carboxylic acid,
IR: $\nu_{max}^{CHCl_3}$ 3300, 1786, 1723, 1680 cm$^{-1}$;
(9) 7-amino-3-cephem-4-carboxylic acid,
mp. 215° C (dec.); and
(10) 7-phenylacetamido-2-methylene-3-cephem-4-carboxylic acid 1-oxide,
mp. 197°-200° C (dec.).

(II) To a mixture of p-nitrobenzyl 7-(2-thienyl)acetamido-3-cephem-4-carboxylate (2.0 g), methanol (40 ml), and tetrahydrofuran (40 ml) one adds 10% hydrochloric acid (1.4 ml) and 5% palladium on carbon (1.9 g), shakes the mixture under hydrogen atmosphere (1 atm.) at room temperature for 2.5 hours, pours into water, extracts with methylene chloride, washes with water, dries, concentrates, and crystallizes from ether to give 7-(2-thienyl)acetamido-3-cephem-4-carboxylic acid (1.30 g).
mp. 174°-175° C. (dec.).

Similarly, the following compounds are prepared from the corresponding p-nitrobenzyl ester.
(1) 7-phenylacetamido-3-cephem-4-carboxylic acid,
mp. 193°-196° C;
(2) 7-phenylacetamido-2-methyl-3-cephem-4-carboxylic acid,
mp. 109°-115° C (dec.);
(3) 7-phenylacetamido-2-methylene-3-cephem-4-carboxylic acid,
Rf: 0.70 (ethyl acetate : acetic acid : water = 8 : 1 : 1/silica gel plate);
(4) 7-phenylacetamido-2-(5-methyl-1,3,4-thiadiazol-2-ylthio)methyl-3-cephem-4-carboxylic acid,
mp. 125°-131° C;
(5) 7-(α-phenylglycyl)amino-3-cephem-4-carboxylic acid,
mp. 180°-210° C (dec.);
(6) 7-(α-phenylglycinamido)-2-methyl-3-cephem-4-carboxylic acid,
mp. 166°-171° C;
(7) 7-thienylacetamido-2-methyl-3-cephem-4-carboxylic acid,
mp. 175°-184° C;
(8) 7-O-formylmandelamido-2-methyl-3-cephem-4-carboxylic acid,
IR: $\nu_{max}^{CHCl_3}$ 3300, 1786, 1723, 1680 cm$^{-1}$; and
(9) 7-amino-3-cephem-4-carboxylic acid,
mp. 215° C (dec.).

PREPARATION 2

Preparation of 7-phenylacetamido-3-chloro-2-methyl-3-cephem-4-carboxylic acid (I) To a solution of p-nitrobenzyl 7-phenylacetamido-3-chloro-3-cephem-4-carboxylate-1-oxide (504 mg) in dimethylformamide (20 ml) one adds a 50% suspension of sodium hydride (48 mg) in mineral oil under nitrogen atmosphere, stirs for 40 minutes, adds methyl iodide (0.5 ml), stirs for 15 minutes at room temperature, dilutes with water, extracts with ethyl acetate, washes with water, dries, concentrates under reduced pressure, and purifies by chromatography to give p-nitrobenzyl 7-phenylacetamido-2-methyl-3-chloro-3-cephem-4-carboxylate-1-oxide (38 mg).

NMR: $\delta^{d_6-DMSO}$: 1.36d(8.0Hz)3H, 3.62s2H, 3.93q(8.0Hz)1H, 4.90d(5.0Hz)1H, 5.40s2H, 5.87dd(5.0;8.0Hz)1H, 7.2–8.4m10H. (II) To a solution of p-nitrobenzyl 7-phenylacetamido-2-methyl-3-chloro-3cephem-4-carboxylate-1-oxide (38 mg) in dimethylformamide (2 ml) one adds stannous chloride dihydrate (44 mg) and acetyl chloride (0.2 ml), stirs for 3hours under ice cooling, adds 5% hydrochloric acid, extracts with ethyl acetate, washes with water, dries, and chromatographs on silica gel to give p-nitrobenzyl 7-phenylacetamido-2-methyl-3-chloro-3cephem-4-carboxylate (29 mg).

IR: $\nu_{max}^{CHCl_3}$ 3420, 1790, 1740, 1690 cm$^{-1}$. (III) One shakes a mixture of p-nitrobenzyl 7phenylacetamido-2-methyl-3-chloro-3cephem-4-carboxylate (27 mg), ethanol (4 ml), and tetrahydrofuran (4ml) in a hydrogen atmosphere with 5% palladium-on-carbon (30 mg) for 2 hours at room temperature, filters to remove solid, concentrates to remove the solvent, dissolves in methylene chloride, extracts with aqueous sodium hydrogen carbonate, acidifies with 5% hydrochloric acid, extracts with ethyl acetate, washes with water, dries, and concentrates to give 7-phhenylacetamido-2-methyl-3-chloro-3-cephem-4-carboxylic acid (14 mg) as a foam.

IR: $\nu_{max}^{CHCl_3}$ 3420, 1790, 1725, 1690 cm$^{-1}$.

What we claim is:

1. A process for preparing compounds having the following formula:

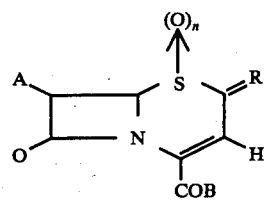

wherein A is amino, mandeloylamino, 0-formylmandeloylamino, phenoxyacetamido, phenylacetamido, α-phenylglycinamido, N-t-butoxycarbonyl-α-phenylglycinamido, or 2-thienylacetamido;

COB is carboxy, p-methoxybenzyloxycarbonyl, p-nitrobenzyloxycarbonyl, 2,2,2-trichloroethoxycarbonyl, or benzhydryloxycarbonyl;

R represets two hydrogens; methyl and hydrogen; (5-methyl-1,3,4-thiadiazol-2yl)thiomethyl and hydrogen; or methylene; and n is zero or one which consists essentially of treating a compound having the following formula:

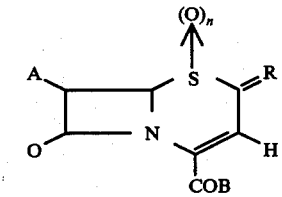

wherein A, COB, R, and n are as defined above and

X is methanesulfonyloxy, benzenesulfonyloxy, toluene-p-sulfonyloxy, chlorine, bromine, or iodine, with a metal selected from the group consisting of zinc, magnesium and aluminum in the presence of acetic acid or a mineral acid or with hydrogen in the presence of a platinum, palladium or nickel catalyst.

2. A process according to claim 1, wherein A is amino, mandeloylamino, phenoxyacetamido, phenylacetamido, α-phenylglycinamido, or 2-thienylacetamido.

3. A process according to claim 1, wherein n is zero.

4. A process according to claim 1, wherein n is one.

5. A process according to claim 1, wherein the reduction is carried out with zinc, magnesium or aluminum in the presence of acetic acid or a mineral acid.

6. A process according to claim 1, wherein the reduction is carried out with hydrogen in the presence of a platinum, palladium or nickel catalyst.

* * * * *

UNITED STATES PATENT AND TRADEMARK OFFICE
CERTIFICATE OF CORRECTION

PATENT NO. : 4,081,595
DATED : March 28, 1978
INVENTOR(S) : Wataru NAGATA et al

It is certified that error appears in the above-identified patent and that said Letters Patent are hereby corrected as shown below:

IN THE HEADING OF THE PATENT:

The third inventor's city:

change "Kyo" to --Kyoto--.

The fourth inventor's first name:

change "Kyoto" to --Kyo--.

Signed and Sealed this

Twenty-second Day of August 1978

[SEAL]

Attest:

RUTH C. MASON
Attesting Officer

DONALD W. BANNER
Commissioner of Patents and Trademarks

UNITED STATES PATENT AND TRADEMARK OFFICE
CERTIFICATE OF CORRECTION

PATENT NO. : 4,081,595

DATED : March 28, 1978

INVENTOR(S) : W. Nagata et al

It is certified that error appears in the above-identified patent and that said Letters Patent are hereby corrected as shown below:

IN THE ABSTRACT:

Page 1, Column 2:

Change the first formula to read:

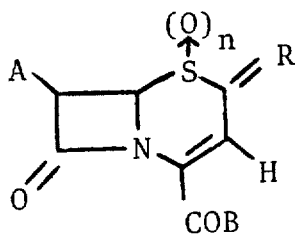

Change the second formula to read:

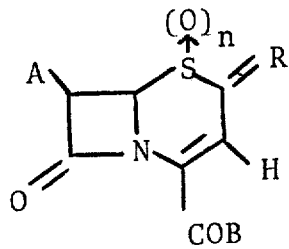

UNITED STATES PATENT AND TRADEMARK OFFICE
CERTIFICATE OF CORRECTION

PATENT NO. : 4,081,595
DATED : March 28, 1978
INVENTOR(S) : W. Nagata et al

It is certified that error appears in the above-identified patent and that said Letters Patent are hereby corrected as shown below:

Column 8:

Change the first formula to read:

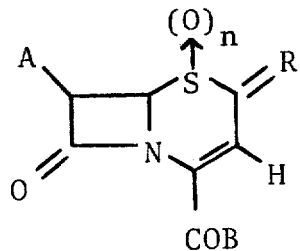

Change the second formula to read:

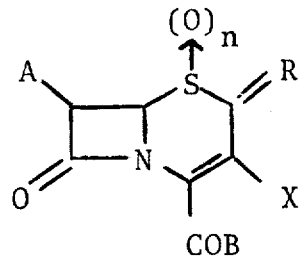

UNITED STATES PATENT AND TRADEMARK OFFICE
CERTIFICATE OF CORRECTION

PATENT NO. : 4,081,595
DATED : March 28, 1978
INVENTOR(S) : W. Nagata et al

It is certified that error appears in the above-identified patent and that said Letters Patent are hereby corrected as shown below:

Column 2, line 24, delete "as"; Column 2, line 49, change "L-0-CO-" to read --L-0-CO-   --;

Column 2, line 53, change "2-alkoxyt-butyl" to read --2-alkoxy-t-butyl--;

Column 5, lines 1 and 16, delete "pO";

Column 7, lines 24, 32 and 35, change "3cephem" to read --3-cephem--; line 35, change "7phenylacetamido" to read --7-phenylacetamido--; line 45, change "7-phhenylacetamido" to read --7-phenylacetamido--;

Signed and Sealed this

Twenty-fourth Day of February 1981

[SEAL]

Attest:

RENE D. TEGTMEYER

Attesting Officer

Acting Commissioner of Patents and Trademarks